United States Patent [19]

Doss et al.

[11] 3,960,138
[45] June 1, 1976

[54] DIFFERENTIAL TEMPERATURE INTEGRATING DIAGNOSTIC METHOD AND APPARATUS

[75] Inventors: James D. Doss; Charles W. McCabe, both of Los Alamos, N. Mex.

[73] Assignee: The United States of America as represented by the United States Energy Research and Development Administration, Washington, D.C.

[22] Filed: Jan. 6, 1975

[21] Appl. No.: 539,130

[52] U.S. Cl. ............................. 128/2 H; 73/342; 324/94
[51] Int. Cl.² ........................................ A61B 5/00
[58] Field of Search ............... 128/2 H, 2.05 R; 324/94; 73/342, 362 AR

[56] References Cited
UNITED STATES PATENTS

| | | | |
|---|---|---|---|
| 3,339,542 | 9/1967 | Howell | 128/2 H |
| 3,623,473 | 11/1971 | Andersen et al. | 128/2 H X |
| 3,651,694 | 3/1972 | Lamb | 128/2 H X |
| 3,688,296 | 8/1972 | Donohue et al. | 324/94 X |
| 3,699,813 | 10/1972 | Lamb | 128/2 H X |
| 3,830,224 | 8/1974 | Vanzetti et al. | 128/2 H |
| 3,847,139 | 11/1974 | Flam | 128/2 H |
| 3,875,505 | 4/1975 | Goldberg | 324/94 |
| 3,878,371 | 4/1975 | Burke | 324/94 X |

*Primary Examiner*—Kyle L. Howell
*Attorney, Agent, or Firm*—Dean E. Carlson; Jerome B. Rockwood

[57] ABSTRACT

A method and device for detecting the presence of breast cancer in women by integrating the temperature difference between the temperature of a normal breast and that of a breast having a malignant tumor. The breast-receiving cups of a brassiere are each provided with thermally conductive material next to the skin, with a thermistor attached to the thermally conductive material in each cup. The thermistors are connected to adjacent arms of a Wheatstone bridge. Unbalance currents in the bridge are integrated with respect to time by means of an electrochemical integrator. In the absence of a tumor, both breasts maintain substantially the same temperature, and the bridge remains balanced. If the tumor is present in one breast, a higher temperature in that breast unbalances the bridge and the electrochemical cells integrate the temperature difference with respect to time.

8 Claims, 3 Drawing Figures

DIFFERENTIAL TEMPERATURE INTEGRATING DIAGNOSTIC METHOD AND APPARATUS

BACKGROUND OF THE INVENTION

It has been medically established that the great majority of malignant mammary tumors act as localized heat sources. The temperature of a breast affected by a malignant tumor remains elevated, while a normal breast fluctuates through a 24 hour temperature cycle. The normal 24 hour temperature cycle comprises a relatively lower temperature during the day and higher temperature at night. The temperature difference between the normal breast and that of a breast containing a malignant tumor provides the basis for the diagnosis of breast cancer by thermographic techniques now in widespread use. The physiological basis is that the malignant process results in a local temperature increase which warms the skin over the general region of the tumor. The present thermography involves the photographing of the breast by means of infrared techniques. The only infrared source is the body heat itself, the higher temperature of the malignancy appearing on the thermograph. While thermography is an effective means for the early diagnosis of breast cancer it is not particularly practical for mass screening of a normal population. A high skilled radiologist is required to analyze the thermograph. In addition, the equipment is expensive and a considerable amount of skilled technician time is required. Furthermore the prospective candidate for diagnosis must be sufficiently motivated to initiate contact with the physician. There is a normal reluctance to do so by those individuals who have no symptoms or who harbor a fear of visiting a physician.

The present invention, while based on the same physiological processes as thermography, is much more suitable for mass screening of the populace. The present invention comprises a temperature-responsive device retained in thermal contact with each breast by means of a brassiere. The brassiere also contains a temperature difference integrator circuit, whereby the difference in mean temperature between the two breasts may be integrated over a period of time. The device is worn for a period of several days in the normal manner, and the integrated temperature difference is then read by a technician. The transaction may be carried out by mail to a central location as will be apparent. Physician time is not required in evaluation of test results. The device readouts may be performed by technicians, and the subject may be contacted by correspondence. Further the cost is apparently low since the brassiere may be reused many times. Only the battery must be replaced regularly. Since the prospective candidate for mass screening need not necessarily visit a physician or any type of medical center to complete the entire test and learn the results, that segment of the population which hesitates to visit a physician can be covered.

It is therefore the object of this invention to provide a method and apparatus for mass screening of the populace for breast malignancies.

DESCRIPTION OF THE PREFERRED EMBODIMENT

Figure 1:
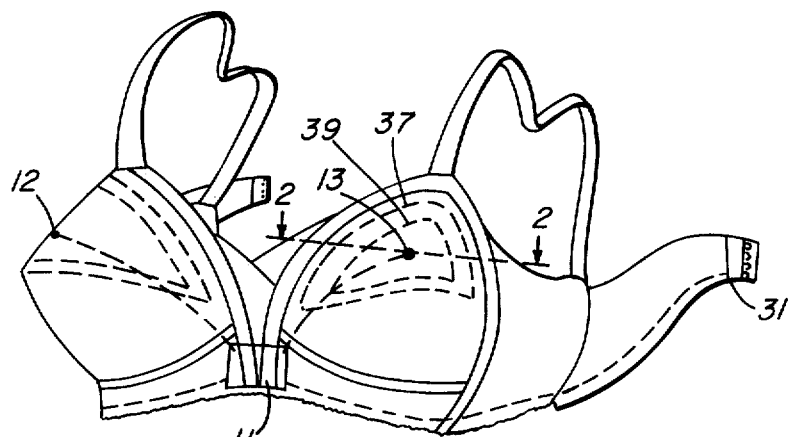
FIG. 1 is a prospective drawing of the brassiere embodying the present invention.
Figure 2:
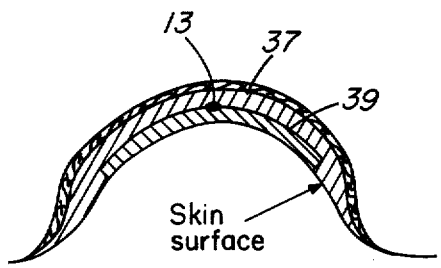
FIG. 2 is a cross section taken along line 2-2 of FIG. 1.

The present invention is incorporated in a substantially conventional brassiere. As illustrated in FIGS. 1 and 2 a thermally conductive sensor pad 39 is placed in the interior of each cup in good thermal contact with the wearer's flesh. Surrounding each sensor pad is a foam insulator 37. Thermistors 12 and 13 are mounted in good thermal contact with thermally conductive sensor pad 39. A printed circuit board containing the circuit 11 of the forming part of the present invention is mounted in the center between the two cups. A switch 31 turns on the cicuitry 11 when the wearer dons the brassiere. When the brassiere is not worn switch 31 remains open.

Figure 3:
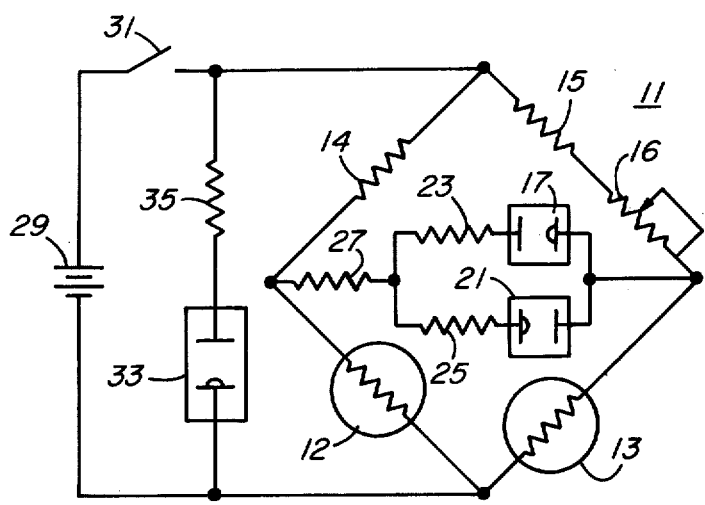
FIG. 3 is a schematic drawing of the circuit employed in connection with the present invention.

The circuit 11 forming part of the present invention is illustrated in FIG. 3. Thermistors 12 and 13 physically positioned as illustrated in FIGS. 1 and 2 are connected in adjacent arms of a Wheatstone bridge as illustrated in FIG. 3. Resistors 14 and 15 are connected in the opposite adjacent arms of the bridge. In addition a balance potentiometer 16 is connected in a series with resistor 15. Electrical energy is supplied to the bridge by battery 29, and controlled by switch 31. The direction and amount of bridge unbalance current is recorded in electrochemical cells 17 and 21 connected with opposite polarity. The relationship between unbalanced voltage and the current passing through the cells is set by resistor 23 in series with electrochemical cell 17, and resistor 25 and in series with electrochemical cell 21 and resistor 27. As illustrated in FIG. 3, resistor 27 is connected to the junction of resistor 14 and thermistor 12 in the bridge, while the working electrode of electrochemical cells 17 and the reservoir electrode of electrochemical cell 21 are connected to the junction between thermistor 13 and potentiometer 16. The period of time the circuit is operative is recorded on a third electrochemical cell 33 connected in series with resistor 35 and in parallel with the bridge, whereby electrochemical cell 33 operates during the time switch 31 is closed and the bridge is operating.

The electrochemical cells 17, 21 and 33 comprise a silver case which serves as the reservoir electrode and a central gold electrode serving as a working electrode. An electrolyte fills the case. When electric current is passed through the electrochemical cell, silver is plated or removed from the gold working anode depending upon the direction of current flow. In the plating mode, one silver atom is deposited per electron on the gold anode while an equal number of silver atoms are removed from the silver case. When electron flow is stopped, the cell will remain in its plated state indefinitely with silver deposited on the gold electrode and a like amount removed from the case. When current flow is reversed silver ions are removed from the gold anode and returned to the silver reservoir. Current flow in both directions is coulometric, since one atom of silver is removed per electron. As will be apparent the flow of silver atoms can continue only until all the silver is removed from the gold electrode.

The present invention is based upon the equation;

$$\overline{\Delta T} = \frac{1}{t} \int_0^t (T_R - T_L) dt, \text{ since } \Delta T = T_R - T_L$$

where $\overline{\Delta T}$ is the mean temperature difference of breast skin, and where t represents time and $T_L$ and $T_R$ are the temperatures of the left and right breast respectively. The integral is measured directly since it is proportional to the charge, i.e., the number of silver ions, transferred through the electrochemical cells during the period of the test. The electrochemical cells 17 and 21 initially have the same quantity $Q_o$ of silver plated on the respective gold working electrodes. Electrochemical cells 17 and 21 therefore begin a measurement period with no difference in plating. Any difference in temperature sensed on the wearer's breasts will unbalance the bridge and cause a current i to flow through resistor 27 and be divided through resistors 23 and 25. This current flow, depending upon direction, will plate silver on one electrochemical cell anode and deplate silver from the other electrochemical cell anode. Therefore, any difference in breast temperature will result in a difference in plating on cells 17 and 21. At the end of a test, each cell is interrogated to determine the precise amount of plating that is present. This information, when combined with the time measurement of electrochemical cell 33 will allow a technician to compute the average difference in breast skin temperature during the diagnostic period.

The bridge is balanced by potentiometer 16 while thermistors 12 and 13 are held at the same temperature. Resistors 23, 25 and 27 are so sized so that combined current $(i_R + i_L)$ through electrochemical cells 17 and 21 will be 0.1 $\mu A/°C$. It will be apparent therefore that the integration of current by electrochemical cells 17 and 21 is equivalent to the integration of the temperature difference between $T_L$ and $T_R$. The instantaneous electron current i flowing through resistor 27 is divided into two components, $i_L$ which flows through resistor 23 and $i_R$ which flows through resistor 25. The mathematical basis for the computation of average temperature is as follows:

$$Q_R = Q_o + \int_o^t i_R \, dt$$

and $$Q_L = Q_o - \int_o^t i_L \, dt$$

where $Q_R$ is the final plating on cell 21 and $Q_L$ is the final plating on cell 17 and where $Q_o$ is the same initial charge plated on cells 21 and 17 and signs are determined by defining a positive electron flow i as left to right through resistor 27.

$$Q_R - Q_L = \int_o^t (i_R + i_L) dt = \int_o^t i \, dt$$

since $i = i_R + i_L$.

But the average current flow through resistor 27 is $$\overline{I} = \frac{1}{t} \int_o^t i \, dt$$

and $\overline{\Delta T} = K\overline{I}$, since $\Delta T = Ki$ where K is a constant of magnitude 10°C/$\mu$A and where $\overline{\Delta T}$ is the average difference in breast temperature and $\Delta T$ is the instantaneous difference in breast temperature sensed by thermistor 12 and 13 with a positive sign assigned for right breast warmer and a negative sign for left breast warmer. From the above expressions it can be seen that:

$$\overline{\Delta T} = \frac{K(Q_R - Q_L)}{t} \begin{cases} \text{positive for right breast warmer} \\ \text{negative for left breast warmer} \end{cases}$$

where $Q_R$ and $Q_L$ have units of microampere-hours and t has units of hours. The magnitude of 10°C per microampere for K is a function of circuit sensitivity determined by design parameters. Since time is an important factor in the equation above, electrochemical cell 33 is provided to measure the actual time that the cancer sensing brassiere of the present invention is actually worn. The charge on electrochemical cell 33 is directly proportional to the time that the circuit is completed by switch 31, which is closed when the brassier clasp is closed.

It is to be clearly understood that the present invention is not limited to the specific features and embodiment set forth herein above but may be carried out in other ways without departing from its spirit.

What we claim is:

1. A method for detecting the presence of a tumor in a human breast comprising the steps of:
    placing a temperature sensing device in thermal contact with each breast;
    measuring the temperature of each breast individually;
    determining the temperature difference between said breasts measuring the time said temperature sensing devices are in thermal contact with said breasts;
    integrating the temperature difference with respect to time; and,
    indicating the integrated temperature difference.

2. In the method set forth in claim 1, mounting said temperature sensing devices in the breast receiving cups of a brassiere.

3. In the method set forth in claim 2, actuating integration and time measurement when a clasp holding said brassiere on the subject is engaged.

4. Apparatus for detecting tumors in the human breast comprising:
    means for simultaneously maintaining a heat-conducting pad in intimate contact with each of a pair of human breasts;
    a temperature responsive resistor in thermal contact with each of said heat-conducting pads;
    a bridge circuit with said temperature responsive resistors connected in circuit in adjacent arms;
    bridge circuit balancing means;
    timing means for determining the time said heat-conducting pads are maintained in contact with said breasts; and,
    current integrating means in circuit with said bridge adapted to provide an indication of cumulative unbalance of said bridge circuit during the time period measured by said timing means as a result of temperature differences between said temperature responsive resistors.

5. In the apparatus set forth in claim 4, said first-mentioned means comprising a brassiere having a pair of breast-receiving cups, each of said cups having a heat conducting pad and a temperature responsive resistor fixed thereto.

6. In the apparatus set forth in claim 5, a circuit closing clasp on said brassiere for actuating said apparatus when said brassiere is normally worn.

7. In the apparatus set forth in claim 6, said temperature responsive resistor comprising thermistors.

8. In the apparatus set forth in claim 7, said timing means comprising a first electrochemical cell, and said integrating means comprising a second electrochemical cell.

* * * * *